US012806309B2

(12) United States Patent
Zhang et al.

(10) Patent No.: US 12,806,309 B2
(45) Date of Patent: Nov. 24, 2026

(54) DEGRADABLE DUAL-COMPONENT HYDROGEL AND ITS PREPARATION AND APPLICATIONS

(71) Applicant: SHANGHAI LINGEL MEDICAL TECHNOLOGY CO., LTD., Shanghai (CN)

(72) Inventors: Yiqing Zhang, Shanghai (CN); Yu Sun, Shanghai (CN)

(73) Assignee: SHANGHAI LINGEL MEDICAL TECHNOLOGY CO., LTD., Shanghai (CN)

( * ) Notice: Subject to any disclaimer, the term of this patent is extended or adjusted under 35 U.S.C. 154(b) by 625 days.

(21) Appl. No.: 18/363,760

(22) Filed: Aug. 2, 2023

(65) Prior Publication Data

US 2023/0372582 A1 Nov. 23, 2023

Related U.S. Application Data

(63) Continuation of application No. PCT/CN2021/091377, filed on Apr. 30, 2021.

(30) Foreign Application Priority Data

Feb. 9, 2021 (CN) ........................ 202110174135.X

(51) Int. Cl.

| | |
|---|---|
| ***A61L 26/00*** | (2006.01) |
| ***A61L 24/00*** | (2006.01) |
| ***A61L 24/04*** | (2006.01) |
| ***A61L 31/04*** | (2006.01) |
| ***A61L 31/14*** | (2006.01) |
| ***C08G 63/91*** | (2006.01) |
| ***C08G 65/333*** | (2006.01) |
| ***C08G 69/50*** | (2006.01) |

(52) U.S. Cl.

CPC ......... *A61L 26/008* (2013.01); *A61L 24/0031* (2013.01); *A61L 24/043* (2013.01); *A61L 26/0052* (2013.01); *A61L 31/041* (2013.01); *A61L 31/145* (2013.01); *C08G 63/912* (2013.01); *C08G 65/33396* (2013.01); *C08G 69/50* (2013.01); *A61L 2400/04* (2013.01)

(58) Field of Classification Search

CPC .. A61L 26/008; A61L 24/0031; A61L 24/043; A61L 26/0052; A61L 31/041; A61L 31/145; A61L 2400/04; C08G 63/912; C08G 65/33396; C08G 69/50

See application file for complete search history.

(56) References Cited

U.S. PATENT DOCUMENTS

2002/0064546 A1 5/2002 Harris

FOREIGN PATENT DOCUMENTS

| | | | |
|---|---|---|---|
| CN | 111440310 | 7/2020 | |
| CN | 111440334 | 7/2020 | |
| CN | 111440334 A * | 7/2020 | ............ C08B 37/08 |
| CN | 111484611 | 8/2020 | |
| CN | 112225912 | 1/2021 | |
| CN | 111621038 | 8/2021 | |

OTHER PUBLICATIONS

Xilong Wu et al., "Synergistic therapeutic effects of Schiff's base cross-linked injectable hydrogels for local co-delivery of metformin and 5-fluorouracil in a mouse colon carcinoma model", Biomaterials, Oct. 2015, pp. 148-162.

Kelly R. Stevens et al., "Degradable hydrogels derived from PEG-diacrylamide for hepatic tissue engineering", Journal of Biomedical Materials Research, Apr. 2015, pp. 3331-3338.

* cited by examiner

*Primary Examiner* — Blessing M Fubara

(74) *Attorney, Agent, or Firm* — JCIPRNET

(57) ABSTRACT

This invention provides the preparation and applications of a degradable dual-component hydrogel. The hydrogel is prepared by mixing component A, component B and solvent; Component A is an o-phthalaldehyde modified degradable polymer; Component B is a water-soluble molecule, a water-soluble synthetic polymer, or a polysaccharide that contains one or more types of the groups selected from primary amine, hydrazine, hydrazide, hydroxylamine and sulfhydryl, with the number of groups not less than 2. This invention achieves the regulation for hydrogel degradability by introducing degradable structures into the polymer skeleton of component A, and obtains hydrogels with rapid degradation. This invention thus solve the dilemma of materials—confronting either the problems of undegradable poly (ethylene glycol) skeleton or the potential risks of the degradable bioproducts introduced—used for preparing the dual-component hydrogel.

7 Claims, 3 Drawing Sheets

DEGRADABLE DUAL-COMPONENT HYDROGEL AND ITS PREPARATION AND APPLICATIONS

CROSS-REFERENCE TO RELATED APPLICATIONS

This application is a continuation of international PCT application Ser. No. PCT/CN2021/091377, filed on Apr. 30, 2021, which claims the priority benefit of China application serial no. 202110174135.X, filed on Feb. 9, 2021. The entirety of each of the above-mentioned patent applications is hereby incorporated by reference herein and made a part of this specification.

TECHNICAL FIELD

The invention belongs to the field of medical material technologies, and specially relates to the preparation and applications of a degradable dual-component hydrogel.

BACKGROUND

A hydrogel is a highly hydrated and crosslinked 3D polymeric networks. Due to its excellent biocompatibility as well as high similarity with the microenvironment of biological tissues, it is widely used in regenerative medicine and tissue engineering. Among various hydrogels, the dual-component hydrogel, which is cross-linked and cured by mixing two reactive gel precursors, can cure in situ, thus possessing excellent tissue integration and having demonstrated good prospects in clinical applications. Currently, products based on injectable dual-component hydrogels are mainly derived from proteins (e.g., Fibrin Glue) and poly (ethylene glycol) (e.g., DuraSeal and CoSeal, etc). The protein-based hydrogels undergo degradation in the presence of corresponding enzymes and can be removed from the affected area, and has excellent degradability. However, these hydrogels confront the disadvantages of the poor mechanical properties, slow curing speed and potential risks for disease transmission. By contrast, poly (ethylene glycol)-based hydrogels have excellent mechanical properties, fast curing speed and have little risk for disease transmission. However, poly (ethylene glycol)-based hydrogels cannot be degraded in vivo due to their stable structure, which has dramatically limited their applications in biomedicine. Hence, it is of great significance to develop a medical hydrogel that features excellent degradability, fast preparation and good biosafety. In Chinese Patent CN202010454896.6, there was a hydrogel preparation technology based on o-phthalaldehyde modified poly (ethylene glycol) or its derivatives (aldehyde components) and modified hyaluronic acid (amino components). The cross-linking method presented in the patent is simple and fast, with mild preparation conditions. However, the aldehyde components are non-degradable, and the degradability of the prepared hydrogel relies closely on the molecular weight of hyaluronic acid. When the molecular weight of hyaluronic acid is high (higher than 340 kDa), the degradation rate of the hydrogel is fairly slow and limits its applications. Based on the same cross-linking method mentioned above, another hydrogel technology was introduced in Chinese Patent CN202010513318.5, which constitutes of the aldehyde components and albumin with inherent amino residues (amino components). The hydrogel prepared with this technology possesses excellent degradability due to the introduction of albumin components. However, this hydrogel takes the risk of disease transmission and biohazardous effects that arise from heterologous proteins, and its clinical applications are also fairly limited.

SUMMARY

Aiming to solve the hard degradation of current poly (ethylene glycol)-based hydrogels, this invention proposes a degradable dual-component hydrogel, as well as its preparation method and applications.

This invention provides degradable aldehyde components by grafting o-phthalaldehyde into the synthetic polymers that contain degradable structures, and further provides the preparation method for a degradable hydrogel by mixing the aldehyde component and an amino-containing component. The proposed method in this invention is simple, with mild preparation conditions and controllable processing time, and the resulting hydrogels feature an adjustable degradation rate and a wide selection range of amino components. In addition, the hydrogels take little risk for disease transmission when used in biological applications.

The objectives of this invention can be realized based on the following technical scheme.

The first objective of this invention is to provide an o-phthalaldehyde modified degradable polymer.

The o-phthalaldehyde modified degradable polymer is composed of two parts: the degradable polymer part denoted as P and the o-phthalaldehyde-based molecule part. The structure is shown in Formula I:

Formula I

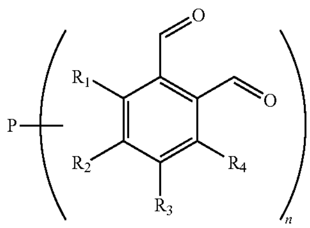

in Formula I,

P is a water-soluble synthetic polymer containing degradable structures, which refers to a biodegradable structure unit. The degradable structure is selected from degradable chemical bonds or degradable polymer segments. The water-soluble synthetic polymer is selected from two-arm poly (ethylene glycol), multi-arm poly (ethylene glycol), poly (propylene glycol), a poly (amino acid), a poly (ethylene glycol)-polytetrahydrofuran copolymer or a poly (ethylene glycol)-poly (propylene glycol) copolymer;

$R_1$, $R_2$, $R_3$, $R_4$ are independently selected from the group consisting of a hydrogen atom, a halogen atom, an amine group, an amino group, a hydroxyl group, a sulphydryl group, a nitro group, a cyano group, an aldehyde group, a ketone group, a carboxyl group, a sulfonic acid group, an alkyl group, an alkylene group, a modified alkyl group, and a modified alkylene group. The modified alkyl group is defined as the alkyl chain that contains double bonds, triple bonds, ether bonds, thioether bonds, imine bonds, ketone bonds, ester bonds, carbonate bonds, thiocarbonate bonds, amide bonds, urethane bonds, or urea bonds. The modified alkylene group is defined as the alkylene chain that contains double bonds, triple bonds, ether bonds, thioether bonds, imine bonds, ketone bonds, ester bonds, carbonate bonds, thiocarbonate bonds, amide bonds, amino bonds, urethane bonds, or urea bonds;

P connects to any one or more groups of $R_1$, $R_2$, $R_3$ and $R_4$ by ether bonds, thioether bonds, ester bonds, carbonate bonds, thiocarbonate bonds, amide bonds, urethane bonds, urea bonds, alkane chains, or modified alkane chains. The modified alkane chain is defined as the alkane chain that contains double bonds, triple bonds, ether bonds, thioether bonds, imine bonds, ketone bonds, ester bonds, carbonate bonds, thiocarbonate bonds, amide bonds, amino bonds, urethane bonds, or urea bonds;

n≥2.

In one preparation method of the invention, the structure of o-phthalaldehyde modified degradable polymer is shown in Formula II:

Formula II

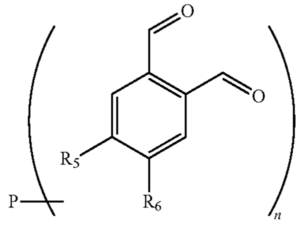

in Formula II,

P is a water-soluble synthetic polymer containing degradable structures. The degradable structure is selected from degradable chemical bonds or degradable polymer segments. The water-soluble synthetic polymer is selected from two-arm poly (ethylene glycol), multi-arm poly (ethylene glycol), poly (propylene glycol), a poly (amino acid), a poly (ethylene glycol)-polytetrahydrofuran copolymer or a poly (ethylene glycol)-poly (propylene glycol) copolymer;

$R_5$, $R_6$ are independently selected from the group consisting of a hydrogen atom, a halogen atom, an amine group, an amino group, a hydroxyl group, a sulphydryl group, a nitro group, a cyano group, an aldehyde group, a ketone group, a carboxyl group, a sulfonic acid group, an alkyl group, an alkylene group, a modified alkyl group, and a modified alkylene group. The modified alkyl group is defined as the alkyl chain that contains double bonds, triple bonds, ether bonds, thioether bonds, imine bonds, ketone bonds, ester bonds, carbonate bonds, thiocarbonate bonds, amide bonds, urethane bonds, or urea bonds. The modified alkylene group is defined as the alkylene chain that contains double bonds, triple bonds, ether bonds, thioether bonds, imine bonds, ketone bonds, ester bonds, carbonate bonds, thiocarbonate bonds, amide bonds, amino bonds, urethane bonds, or urea bonds;

P connects to any one or two groups of $R_5$ and $R_6$ by ether bonds, thioether bonds, ester bonds, carbonate bonds, thiocarbonate bonds, amide bonds, urethane bonds, urea bonds, alkane chains, or modified alkane chains. The modified alkane chain is defined as the alkane chain that contains double bonds, triple bonds, ether bonds, thioether bonds, imine bonds, ketone bonds, ester bonds, carbonate bonds, thiocarbonate bonds, amide bonds, amino bonds, urethane bonds, or urea bonds;

n≥2.

In one preparation method of the invention, the degradable chemical bond is selected from ester bonds, carbonate bonds, or thiocarbonates;

The degradable polymer segment is selected from polycarbonate, polyester, a poly (amino acid), or a polypeptide;

The polyester includes, but is not limited to, a poly (lactic acid), a poly (lactic acid-co-glycolic acid) copolymer, or polycaprolactone.

In one preparation method of the invention, P is selected from:

a degradable structure terminated poly (ethylene glycol), a copolymer of poly (lactic acid) and poly (ethylene glycol), a copolymer of polycaprolactone and poly (ethylene glycol), a copolymer of poly (ethylene glycol), poly (lactic acid) and poly (glycolic acid), and a poly (amino acid).

In one preparation method of the invention, when P is the degradable structure terminated poly (ethylene glycol), the Formula II is selected from the following structures (Component A-1 to A-3):

Component A-1

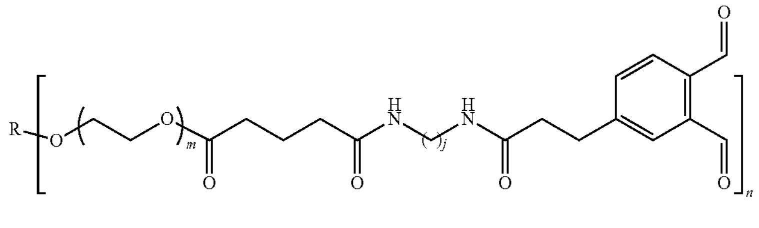

Component A-2

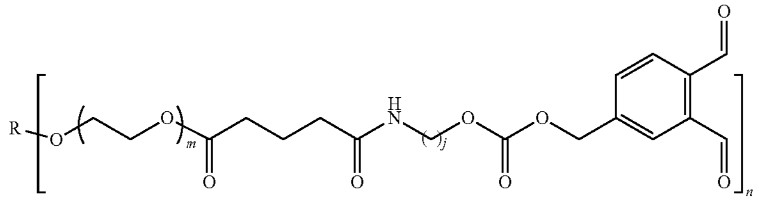

-continued
Component A-3
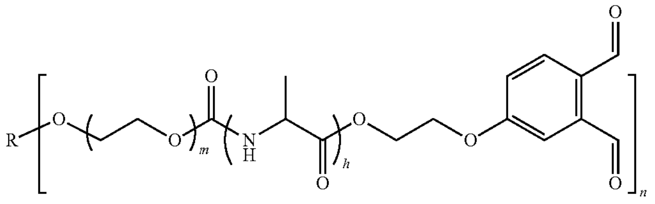
When P is the copolymer of poly (lactic acid) and poly (ethylene glycol), the Formula II is selected from the following structures (Component A-4 to A-7):
Component A-4
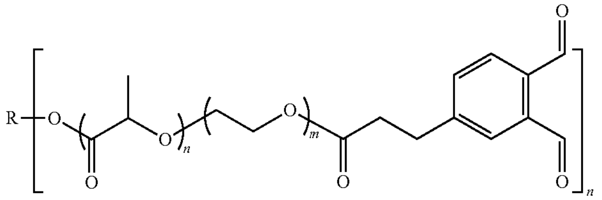
Component A-5
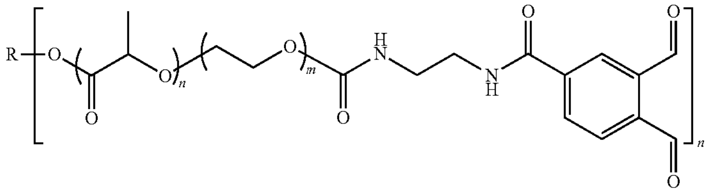
Component A-6
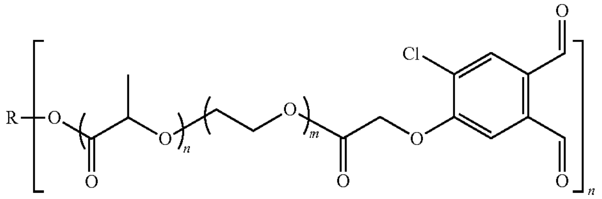
Component A-7
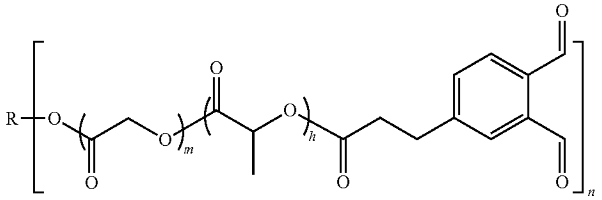
When P is the copolymer of polycaprolactone and poly (ethylene glycol), the Formula II has the following structure (Component A-8):
Component A-8
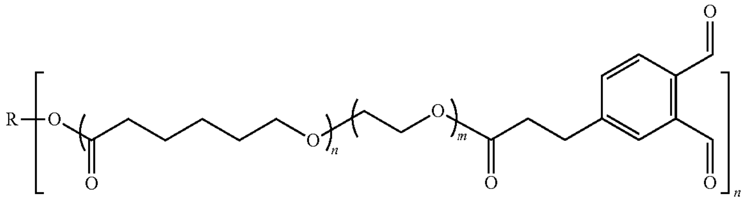

When P is the copolymer of poly (ethylene glycol), poly (lactic acid) and poly (glycolic acid), the Formula II has the following structure (Component A-9):

Component A-9

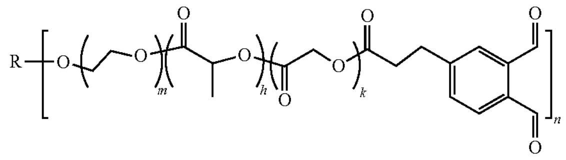

When P is the poly (amino acid), the Formula II has the following structure (Component A-10):

Component A-10

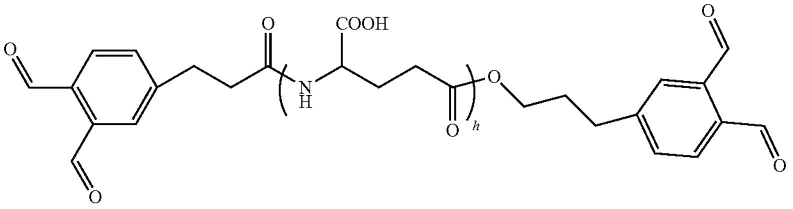

In above structures, j, m, h, and k represent the numbers of repeating units ($1 \leq j \leq 30$, $5 \leq m \leq 1000$, $2 \leq h \leq 1000$, $2 \leq k \leq 3000$);

n represents the branching degree of the multi-arm polymer, selected from 2, 3, 4, 5, 6, or 8;

R is a two-arm branching center (n=2), selected from one of the following structures:

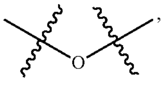
,
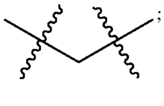
;

R is a three-arm branching center (n=3), selected from one of the following structures:

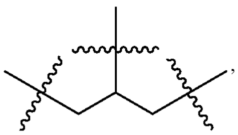
,
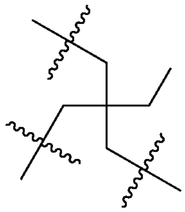
,
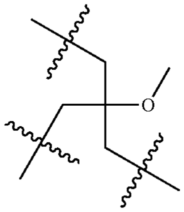
;

R is a four-arm branching center (n=4), selected from one of the following structures:

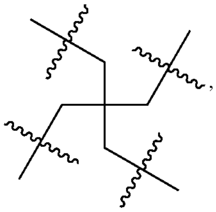
,
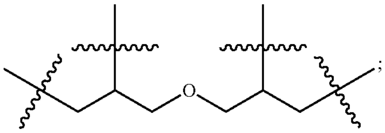
;

R is a five-arm branching center (n=5), selected from one of the following structures:

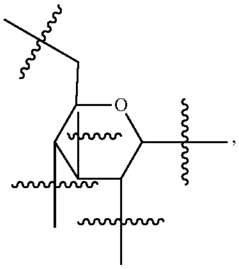
,
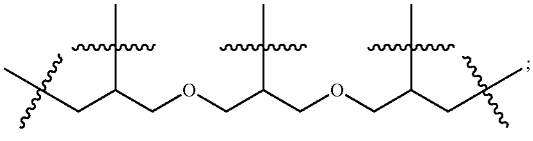
;

R is a six-arm branching center (n=6), selected from one of the following structures:

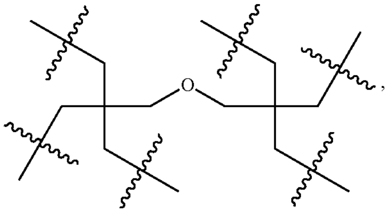
,

-continued

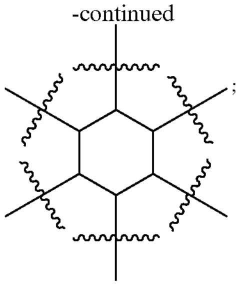

;

R is an eight-arm branching center (n=8), selected from one of the following structures:

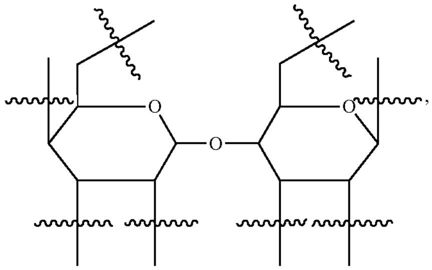

,

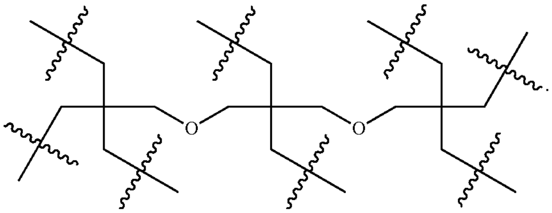

.

The second objective of this invention is to provide a degradable dual-component hydrogel, which is prepared by mixing component A, component B, and solvent;

Component A is the o-phthalaldehyde modified degradable polymer.

Component B is a water-soluble small molecule, water-soluble synthetic polymer or polysaccharide that contains one or more types of groups selected from primary amine, hydrazine, hydrazide, hydroxylamine, and sulfhydryl, with the number of groups not less than 2.

In one preparation method of the invention, component B is selected from the amino acid compounds containing multiple amino groups (e.g., polylysine), lysine-modified two-arm or multi-arm poly (ethylene glycol), amino-terminated two-arm or multi-arm poly (ethylene glycol), lysine-modified hyaluronic acid, hydrazide-modified hyaluronic acid or hydrazide-modified chitosan.

In one preparation method of the invention, the solvent is selected from water, physiological saline, buffer solution, acellular matrix, or cell culture medium solution.

The third objective of this invention is to provide the preparation method of the degradable dual-component hydrogel: Component A and component B are dissolved in the solvent to obtain solution A and solution B, respectively. The solution A and B are mixed to obtain a hydrogel.

In one preparation method of the invention, in solution A, the solid content of component A is 0.5-20 wt %; in solution B, the solid content of component B is 0.1-20 wt %.

In one preparation method of the invention, preferably, the preparation temperature of the hydrogel is 0-80 °C; the preparation pH is 3-12.

The fourth objective of this invention is to provide applications of the degradable component hydrogel, which are selected from:

The use of the degradable dual-component hydrogel for preparing repair-promoting materials after cervical surgery;

The use of the degradable dual-component hydrogel for preparing materials to prevent postoperative peritoneal adhesion;

The use of the degradable dual-component hydrogel for preparing materials to seal intestinal leakage;

The use of the degradable dual-component hydrogel for preparing hepatic hemostatic materials;

The use of the degradable dual-component hydrogel for preparing cardiac hemostatic materials;

The use of the degradable dual-component hydrogel for preparing materials to repair dura mater spinalis wound;

The use of the degradable dual-component hydrogel for preparing materials to repair dura mater wound;

The use of the degradable dual-component hydrogel for preparing materials to seal blood vessels.

Compared with the prior technologies, this invention provides a degradable dual-component hydrogel prepared by mixing component A, component B, and solvent. Component A is an aldehyde-containing component. Component B is an amino-containing component. This invention achieves the regulation of hydrogel degradability by introducing degradable structures into the polymer skeleton of component A, and obtains hydrogels with rapid degradation. This invention thus solves the dilemma of materials—confronting either the problems of undegradable poly (ethylene glycol) skeleton or the potential risks of the degradable bioproducts introduced—used for preparing the dual-component hydrogel. Moreover, the method presented for hydrogel preparation in this invention is simple, with mild processing conditions and controllable processing time. There is no additional modification needed for the amino components in this method, so the selection of amino components is fairly wide. It can be concluded that the prepared hydrogels display high promise for biomedical applications.

DETAILED DESCRIPTION

Figure 1:
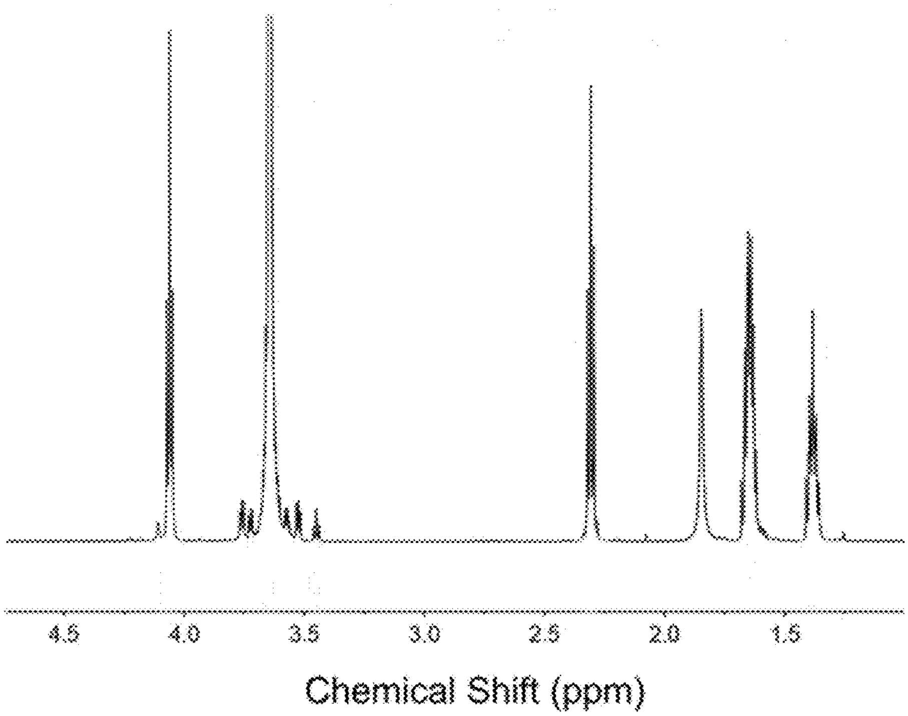
FIG. 1 is the $^{1}H$ NMR spectra of polycaprolactone-poly (ethylene glycol) copolymer in Embodiment 8.

This invention will be described in detail in combination with drawings and specific embodiments.

Embodiment 1: Synthesis of the Representative Compound of Component A-1 (Component A-1.1; j=6, m=230, n=4)

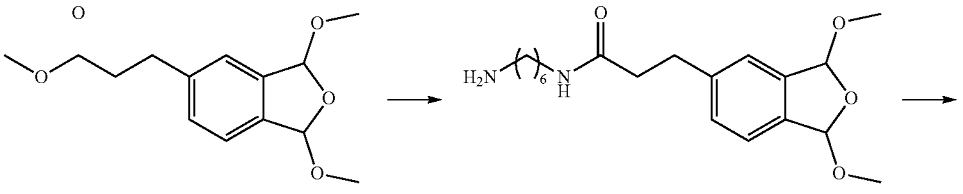

Compound 1 Compound 2

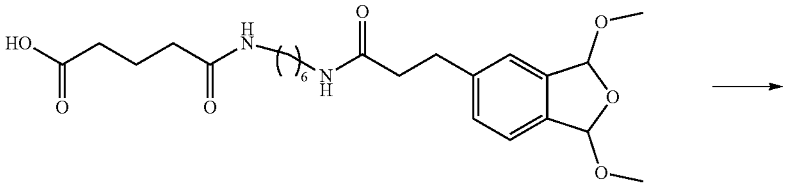

Compound 3

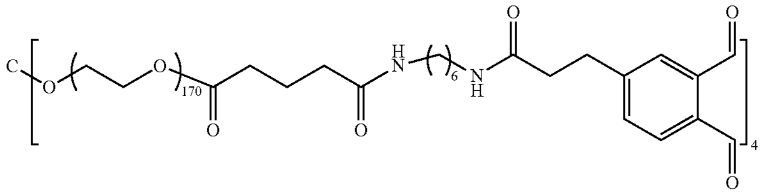

Compound A-1.1

(1) Synthesis of Compound 1: The synthesis was carried out according to the method referred to in the reference (Chun Ling Tung, Clarence T. T. Wong, Eva Yi Man Fung and Xuechen Li. Org. Lett. 2016, 18, 11, 2600-2603). $^1$H NMR (400 MHz, $CDCl_3$) δ=7.30 (m, 2H), 7.23 (s, 1H), 6.29 (s, 1H), 6.03 (s, 1H), 3.66 (s, 3H), 3.43 (m, 6H), 3.00 (t, J=7.7, 2H), 2.63 (t, J=7.7, 2H).

(2) Synthesis of Compound 2: Compound 1 (1.0 g) and hexanediamine (4.36 g) were dissolved in methanol (5 mL) and stirred at room temperature for 2 h. Remove most of the solvent after reaction completed, extract residual compounds with ethyl acetate (EA) for three times and collect organic phase. The organic phase was dried by anhydrous $Na_2SO_4$ and the solvent was removed by vacuum distillation to collect crude products, which were purified by silica gel column chromatography to obtain Compound 2 (1.04 g, yield: 80%). $^1$H NMR (400 MHz, $CDCl_3$): δ=7.30 (m, 2H), 7.22 (s, 1H), 6.29 (s, 1H), 6.04 (s, 1H), 3.44 (m, 6H), 3.01 (t, J=7.6, 2H), 2.69 (m, 2H), 2.50 (m, 4H), 1.52 (m, 2H), 1.30 (m, 6H).

(3) Synthesis of Compound 3: Compound 2 (1.0 g) was dissolved in 6 mL of anhydrous tetrahydrofuran (THF), with the addition of glutaric anhydride (0.46 g). The above solution was stirred at room temperature for 2 h. Add water after reaction completed, extract residual compounds with EA for three times and collect organic phase. The organic phase was dried by anhydrous $Na_2SO_4$ and the solvent was removed by vacuum distillation to collect crude products, which were purified by silica gel column chromatography to obtain Compound 3 (1.12 g, yield: 65%). $^1$H NMR (400 MHz, $CDCl_3$): δ=7.30 (m, 2H), 7.22 (s, 1H), 6.29 (s, 1H), 6.04 (s, 1H), 3.60 (m, 4H), 3.44 (m, 6H), 3.01 (t, J=7.6, 2H), 2.69 (m, 4H), 2.50 (m, 4H), 1.52 (m, 2H), 1.30 (m, 6H).

(4) Synthesis of Component A-1.1: Compound 3 (0.97 g) and 1-ethyl-3-(3-dimethylaminopropyl) carbodiimide (EDC; 0.40 g) were dissolved in anhydrous dichloromethane (DCM, 20 mL) and stirred for 10 min. Add dropwise the mixed solution of anhydrous DCM dissolved with four-arm poly (ethylene glycol) (Mw: 40 kDa; 3.5 g) and 4-dimethylaminopyridine (DMAP; 0.02 g) into the above solution. The solution was stirred at room temperature for 5 h. Extract unreacted raw materials (e.g., Compound 2) with DCM and water, and collect the products in organic phase. Remove most of the solvent by vacuum distillation and pour the residue into ethyl ether ($Et_2O$) to collect white solid (3.4 g). The dried solid was redissolved in anhydrous DCM (20 mL) with the addition of trifluoroacetic acid (TFA; 0.3 mL). The above solution was stirred at room temperature for 2 h and washed three times with extra DCM and saturated $NaHCO_3$ solution, and then dried. Remove most of the solvent by vacuum distillation, pour the residue into $Et_2O$ and collect white solid by filtration. The solid was dried to obtain Component A-1.1 (3.2 g, yield: 90%). According to $^1$H NMR spectroscopy, the peaks at 7.2-7.5 ppm belong to the protons in benzene ring, and the grafting degree (3.4-3.6) can be calculated by the integral ratio between above peaks and the peaks of protons in poly (ethylene glycol) skeleton. $^1$H NMR (400 MHz, $D_2O$): δ=10.57 (s, 4H), 10.48 (s, 4H), 7.80 (m, 8H), 7.66 (m, 4H), 3.72 (m, 3636H), 3.01 (t, J=7.6, 8H), 2.69 (m, 16H), 2.50 (m, 8H), 1.52 (m, 8H), 1.30 (m, 24H).

Embodiment 2: Synthesis of the Representative Compound of Component A-2 (Component A-2.1; j=6, m=230, n=4)

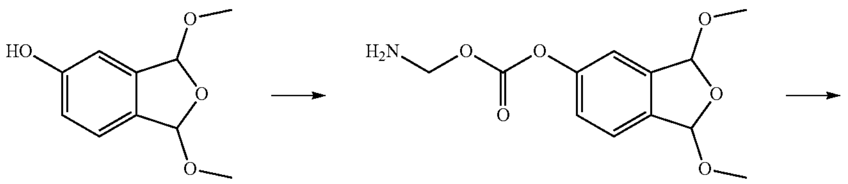

Compound 4 Compound 5

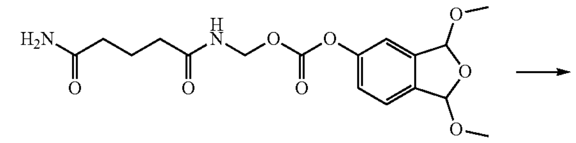

Compound 6

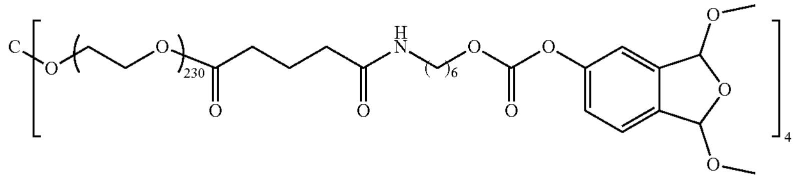

Compound A-2.1

(1) Synthesis of Compound 4: The synthesis was carried out according to the method referred to in the reference (Schmidt P, Zhou L, Tishinov K, et al. Dialdehydes Lead to Exceptionally Fast Bioconjugations at Neutral pH by Virtue of a Cyclic Intermediate. Angewandte Chemie International Edition, 2014, 53, 10928-10931). $^1$H NMR (400 MHz, $D_6$-DMSO) δ=8.05 (d, J=7.6 Hz, 1H), 7.93 (s, 1H), 7.81 (br.s, 1H), 7.55 (d, J=7.6 Hz, 1H), 6.36 (s, 1H), 6.11 (s, 1H), 3.66 (s, 3H), 3.37-3.32 (m, 6H).

(2) Synthesis of Compound 5: 6-amino-1-hexanol (0.5 g) was dissolved in anhydrous DCM, with the addition of triethylamine (TEA; 0.87 mL) and DMAP (50 mg) for catalysis. The above solution was dropwise added into the solution of anhydrous DCM dissolved with 4-nitrophenyl chloroformate (1.7 g). The solution was stirred at room temperature for 5 h. After reaction completed, remove the organic solvent to collect crude products for the next reaction. The crude products were dried and redissolved in anhydrous DCM, with the addition of Compound 4 (1 g). The above solution was stirred at room temperature for 2 h and then its solvent was removed. The products were purified by silica gel column chromatography to obtain Compound 5 (1.3 g, yield: 90%). $^1$H NMR (400 MHz, $CDCl_3$): δ=7.50 (m, 2H), 7.20 (s, 1H), 6.29 (s, 1H), 6.02 (s, 1H), 3.44 (m, 6H), 3.01 (t, J=7.6, 2H), 2.69 (m, 2H), 1.52 (m, 2H), 1.30 (m, 6H).

(3) Synthesis of Compound 6: Refer to the synthetic method of Compound 3. $^1$H NMR (400 MHz, $CDCl_3$): δ=7.50 (m, 2H), 7.22 (s, 1H), 6.29 (s, 1H), 6.04 (s, 1H), 3.44 (m, 6H), 3.01 (t, J=7.6, 2H), 2.69 (m, 4H), 1.52 (m, 2H), 1.30 (m, 6H).

(4) Synthesis of Component A-2.1: Refer to the synthetic method of Component A-1.1. According to $^1$H NMR spectroscopy, the peaks at 7.2-7.5 ppm belong to the protons in benzene ring, and the grafting degree (3.4-3.6) can be calculated by the integral ratio between above peaks and the peaks of protons in poly (ethylene glycol) skeleton. $^1$H NMR (400 MHz, $D_2O$): δ=10.60 (s, 4H), 10.52 (s, 4H), 7.90 (m, 8H), 7.79 (s, 4H), 3.72 (m, 3636H), 3.01 (t, J=7.6, 16H), 2.69 (m, 16H), 1.52 (m, 8H), 1.30 (m, 24H).

Embodiment 3: Synthesis of the Representative Compound of Component A-3 (Component A-3.1; j=6, m=230, n=4)

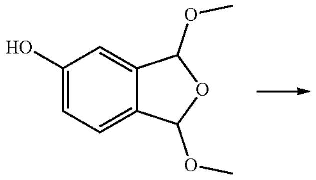

Compound 7

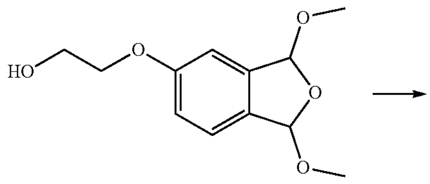

Compound 8

-continued

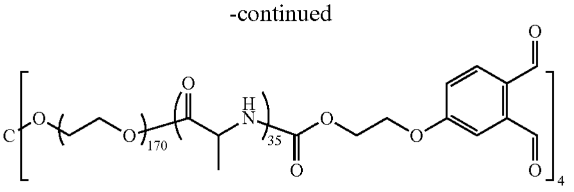

Compound A-3.1

(1) Synthesis of Compound 7: The synthesis was carried out according to the method referred to in the reference (Schmidt P, Zhou L, Tishinov K, et al. Dialdehydes Lead to Exceptionally Fast Bioconjugations at Neutral pH by Virtue of a Cyclic Intermediate. Angewandte Chemie International Edition, 2014, 53, 10928-10931). $^1$H NMR (400 MHz, $D_6$-DMSO) δ=8.05 (d, J=7.6 Hz, 1H), 7.93 (s, 1H), 7.81 (br.s, 1H), 7.55 (d, J=7.6 Hz, 1H), 6.36 (s, 1H), 6.11 (s, 1H), 3.66 (s, 3H), 3.37-3.32 (m, 6H).

(2) Synthesis of Compound 8: Compound 7 (1 g) was dissolved in anhydrous N, N-dimethylformamide (DMF), with the addition of 2-bromoethanol (0.87 mL) and twice molar equivalent of potassium carbonate (1.2 g). The solution was stirred at room temperature for 5 h. After reaction completed, remove the organic solvent to collect crude products, which were purified by silica gel column chromatography to obtain Compound 8 (1.3 g, yield: 90%). $^1$H NMR (400 MHz, $CDCl_3$) δ=7.81 (brs, 1H), 7.50 (m, 2H), 7.23 (s, 1H), 6.29 (s, 1H), 6.03 (s, 1H), 3.95 (t, J=4.8 Hz, 2H), 3.81 (m, 2H), 3.43 (m, 6H), 2.86 (brs, 1H).

(3) Synthesis of Component A-3.1: Compound 8 (0.4 g) was dissolved in anhydrous DCM (100 mL), with the addition of TEA (0.162 g) and 4-Dimethylaminopyridine (DMAP; 0.0012 g). The above solution was dropwise added into the anhydrous DCM (5 mL) dissolved 4-nitrophenyl chloroformate (0.322 g). The solution was stirred at room temperature for 5 h. Remove the solvent by vacuum distillation and purify products by silica gel column chromatography to obtain an intermediate product (0.35 g). The intermediate product was dried and redissolved in anhydrous DMF (50 mL), with the addition of TEA (0.1 mL) and poly (lactic acid)-poly (ethylene glycol) copolymer (8 g). Stir the mixture at room temperature for 6 h and remove the solvent by vacuum distillation. The mixture was redissolved in deionized water, dialyzed to remove small molecular impurities, and lyophilized. The product was redissolved in anhydrous DCM (20 mL) with 10% TFA. The above solution was stirred at room temperature for 12 h. Remove TFA by vacuum distillation, dissolve the residue in DCM, pour the solution into $Et_2O$ and collect light yellow solid (i.e., Component A-3.1; 7.2 g, yield: 90%). According to $^1$H NMR spectroscopy, the peaks at 7.8 and 7.6 ppm belong to the protons in benzene ring, and the grafting degree (3.4-3.6) can be calculated by the integral ratio between above peaks and the peaks of protons in poly (ethylene glycol) skeleton. $^1$H NMR (400 MHz, $D_2O$): δ=3.72 (s, 2727H), 1.52 (m, 420H), 10.57 (s, 4H), 10.48 (s, 4H), 7.50 (m, 8H), 7.20 (s, 4H), 3.95 (t, J=4.8 Hz, 8H), 3.81 (m, 8H).

Embodiment 4: Synthesis of the Representative Compound of Component A-4 (Component A-4.1; h=35, m=170, n=4)

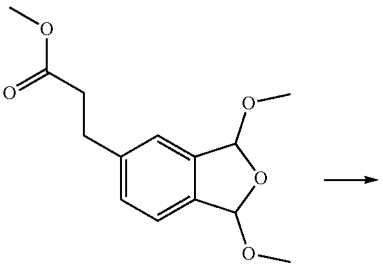

Compound 1

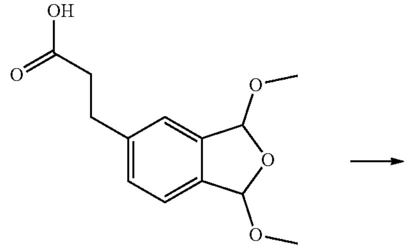

Compound 9

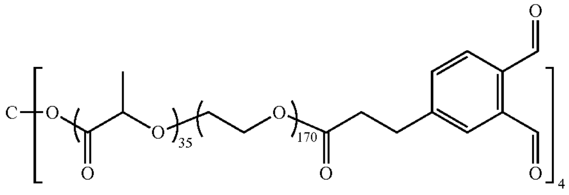

Compound A-4.1

(1) Synthesis of Compound 9: Compound 1 (2.0 g) was dissolved in methanol, with the addition of 10% NaOH aqueous solution (5 mL). The solution was stirred at room temperature for 4 h. Remove the methanol by vacuum distillation and adjust the pH to 2 by adding HCl aqueous solution (1M). Extract residual compounds with DCM for three times and collect the organic phase. The organic phase was dried by anhydrous $Na_2SO_4$ and the solvent was removed by vacuum distillation to collect crude products, which were purified by silica gel column chromatography to obtain Compound 9 (1.43 g, yield: 80%). $^1$H NMR (400 MHz, $CDCl_3$): δ=7.31 (m, 2H), 7.24 (s, 1H), 6.29 (s, 1H), 6.04 (s, 1H), 3.44 (m, 6H), 3.01 (t, J=7.6, 2H), 2.68 (t, J=7.8, 2H).

(2) Synthesis of Component A-4.1: Refer to the synthetic method of component A-2.1. According to $^1$H NMR spectroscopy, the peaks at 7.2 and 7.3 ppm belong to the protons in benzene ring and the grafting degree (3.4-3.6) can be calculated by the integral ratio between above peaks and the peaks of protons in poly (ethylene glycol) skeleton. $^1$H NMR (400 MHz, $D_2O$): δ=3.72 (s, 2727H), 5.23 (m, 140H), 1.62 (d, 420H), 10.48 (s, 4H), 7.32 (m, 8H), 7.31 (m, 8H), 7.24 (s, 4H), 3.01 (t, J=7.6, 8H), 2.68 (t, J=7.8, 8H).

Embodiment 5: Synthesis of the Representative Compound of Component A-5 (Component A-5.1; h=35, m=170, n=4)

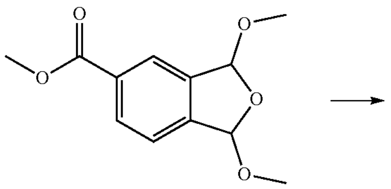

Compound 10

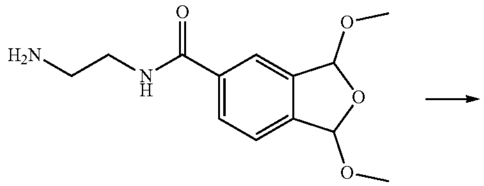

Compound 11

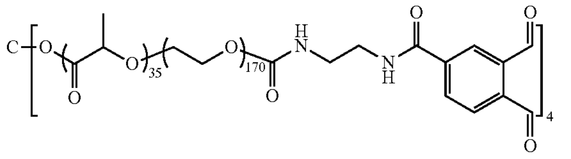

Compound A-5.1

(1) Synthesis of Compound 10: Refer to the synthetic method of Compound 7. $^1$H NMR (400 MHz, $D_6$-DMSO) δ=13.21 (br. s, 1H), 8.05 (d, J=7.6 Hz, 1H), 7.93 (s, 1H), 7.55 (d, J=7.6 Hz, 1H), 6.36 (s, 1H), 6.11 (s, 1H), 3.37-3.32 (m, 6H).

(2) Synthesis of Compound 11: Compound 10 (1.0 g) and ethylenediamine (4.36 g) were dissolved in methanol (5 mL). The solution was stirred at room temperature for 2 h. Remove most of the solvent after reaction completed, extract residual compounds with EA for three times and collect the organic phase. The organic phase was dried by anhydrous $Na_2SO_4$ and the solvent was removed by vacuum distillation to collected crude products, which were purified by silica gel column chromatography to obtain Compound 11 (1.04 g, yield: 80%). $^1$H NMR (400 MHz, $CDCl_3$): δ=8.05 (d, J=7.6 Hz, 1H), 7.93 (s, 1H), 7.55 (d, J=7.6 Hz, 1H), 6.29 (s, 1H), 6.04 (s, 1H), 3.60 (m, 4H), 3.44 (m, 6H), 1.52 (m, 2H), 1.30 (m, 6H).

(3) Synthesis of Component A-5.1: Poly (lactic acid)-poly (ethylene glycol) copolymer (8 g) was dissolved in anhydrous DCM (100 mL), with the addition of DMAP (0.0012 g) and TEA (0.162 g). The above solution was dropwise added into the anhydrous DCM (5 mL) dissolved 4-nitrophenyl chloroformate (0.322 g). The solution was stirred at room temperature for 5 h. Remove half of the solvent by vacuum distillation, pour the residue into $Et_2O$, and collect white solid by filtration. Repeat the above process until unreacted raw materials (e.g., 4-nitrophenyl chloroformate) are completely removed, thus obtaining an intermediate product (7.8 g). The intermediate product was dried and redissolved in anhydrous DMF (50 mL), with the addition of TEA (0.1 mL) and compound 1 (0.397 g). Stir the mixture at room temperature for 6 h and remove the solvent by vacuum distillation. The mixture was redissolved in deionized water, dialyzed to remove small molecular impurities, and lyophilized. The product was redissolved in anhydrous DCM with 10% TFA. The above solution was stirred at room temperature for 12 h. Remove TFA by vacuum distillation, dissolve the residue in DCM, pour the solution into $Et_2O$ and collect light yellow solid (i.e., Component A-5.1; 7.2 g, yield: 90%). According to $^1$H NMR spectroscopy, the peaks at 7.8 and 7.6 ppm belong to the protons in benzene ring, and the grafting degree (3.4-3.6) can be calculated by the integral ratio between above peaks and the peaks of protons in poly (ethylene glycol) skeleton. $^1$H NMR (400 MHz, $D_2O$): δ=10.57 (s, 4H), 10.48 (s, 4H), 7.80 (m, 8H), 7.66 (m, 4H), 3.72 (s, 2727H), 5.23 (m, 140H), 1.62 (d, 420H), 3.60 (m, 16H).

Embodiment 6: Synthesis of the Representative Compound of Component A-6 (Component A-6.1; h=35, m=170, n=4)

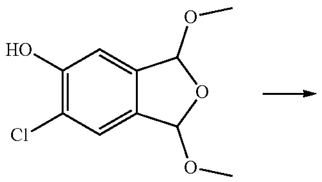

Compound 12

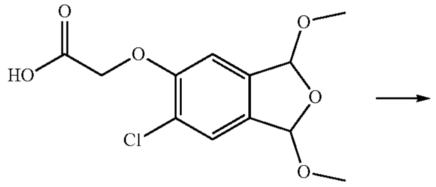

Compound 13

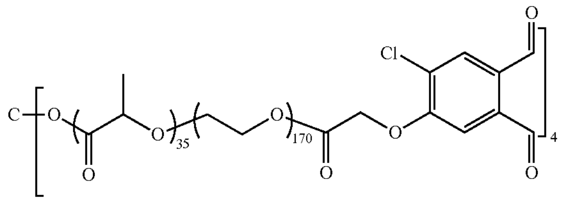

Compound A-6.1

(1) Synthesis of Compound 12: Refer to the synthetic method of Compound 7. $^1$H NMR (400 MHz, $CDCl_3$): $^1$H NMR (400 MHz, $CDCl_3$) δ=7.49 (s, 1H), 6.94 (s, 1H), 6.29 (s, 1H), 6.03 (s, 1H), 3.43 (m, 6H).

(2) Synthesis of Compound 13: Compound 12 (1 g) was dissolved in anhydrous DMF, with the addition of bromoacetic acid (0.87 mL) and twice molar equivalent of potassium carbonate (1.2 g). The solution was stirred at room temperature for 5 h. After reaction completed, remove the organic solvent to collect crude products, which were purified by silica gel column chromatography to obtain Compound 13 (1.3 g, yield: 90%). $^1$H NMR (400 MHz, $CDCl_3$): δ=7.64 (m, 1H), 7.02 (s, 1H), 6.29 (s, 1H), 6.03 (s, 1H), 3.63 (m, 4H), 3.03 (t, J=7.6, 2H).

(3) Synthesis of Component A-6.1: Refer to the synthetic method of Component A-2.1. According to $^1$H NMR spectroscopy, the peaks at 7.6 and 7.0 ppm belong to the protons in benzene ring and the grafting degree (3.4-3.6) can be calculated by the integral ratio between above peaks and the peaks of protons in poly (ethylene glycol) skeleton. $^1H$ NMR (400 MHz, $D_2O$): δ=10.58 (s, 4H), 10.52 (s, 4H), 7.80 (m, 4H), 7.70 (s, 4H), 3.72 (s, 2727H), 5.23 (m, 140H), 1.62 (d, 420H), 3.01 (t, J=7.6, 8H).

Embodiment 7: Synthesis of the Representative Compound of Component A-7 (Component A-7.1; h=35, m=170, n=4)

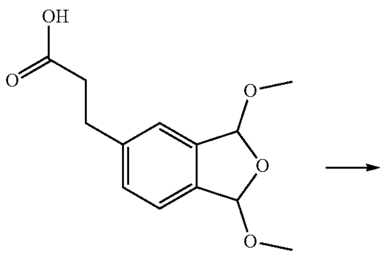

Compound 9

-continued

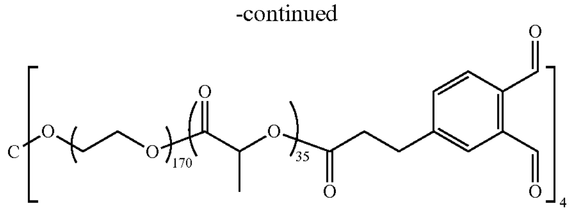

Compound A-7.1

(1) Synthesis of Component A-7.1: Refer to the synthetic method of Component A-2.1. According to $^1H$ NMR spectroscopy, the peaks at 7.2 and 7.3 ppm belong to the protons in benzene ring and the grafting degree (3.4-3.6) can be calculated by the integral ratio between above peaks and the peaks of protons in poly (ethylene glycol) skeleton. $^1H$ NMR (400 MHz, $D_2O$): δ=3.72 (s, 2727H), 5.23 (m, 140H), 1.62 (d, 420H), 10.48 (s, 4H), 7.32 (m, 8H), 7.31 (m, 8H), 7.24 (s, 4H), 3.01 (t, J=7.6, 8H), 2.68 (t, J=7.8, 8H).

Embodiment 8: Synthesis of the Representative Compound of Component A-8 (Component A-8.1; h=20, m=170, n=4)

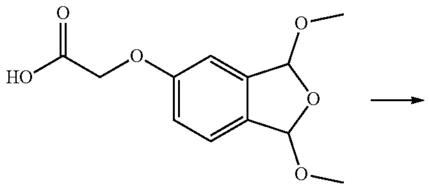

Compound 9

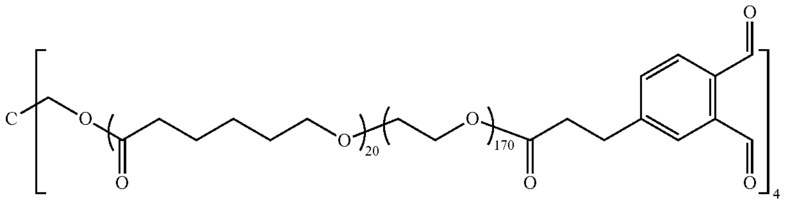

Compound A-8.1

(1) Synthesis of Component A-8.1: Refer to the synthetic method of Component A-2.1. According to $^1H$ NMR spectroscopy, the peaks at 7.2 and 7.3 ppm belong to the protons in benzene ring and the grafting degree (3.4-3.6) can be calculated by the integral ratio between above peaks and the peaks of protons in poly (ethylene glycol) skeleton. $^1H$ NMR (400 MHz, $D_2O$): δ=4.21 (t, 170H), 3.72 (s, 2727H), 2.42 (m, 170H), 1.54 (m, 340H), 1.47 (m, 170H), 10.57 (s, 4H), 10.48 (s, 4H), 7.30 (m, 8H), 7.20 (s, 4H), 3.60 (m, 16H), 3.01 (t, J=7.6, 8H), 2.65 (t, J=7.6, 8H).

Embodiment 9: Synthesis of the Representative Compound of Component A-9 (Component A-9.1; h=35, m=115, k=45, n=4)

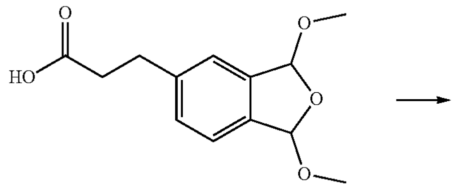

Compound 9

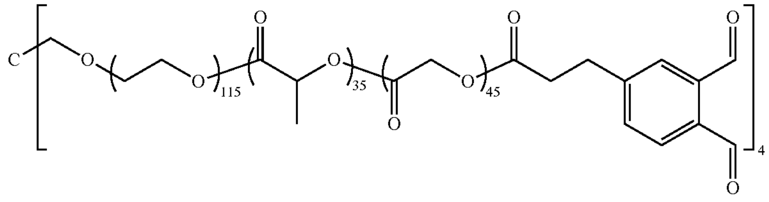

Compound A-9.1

(1) Synthesis of Component A-9.1: Refer to the synthetic method of Component A-2.1. According to $^1H$ NMR spectroscopy, the peaks at 7.2 and 7.3 ppm belong to the protons in benzene ring and the grafting degree (3.4-3.6) can be calculated by the integral ratio between above peaks and the peaks of protons in poly (ethylene glycol) skeleton. $^1H$ NMR (400 MHz, $D_2O$): δ=3.72 (s, 1818H), 5.23 (m, 140H), 1.62 (d, 420H), 4.85 (s, 340H), 10.48 (s, 4H), 7.32 (m, 8H), 7.31 (m, 8H), 7.24 (s, 4H), 3.01 (t, J=7.6, 8H), 2.68 (t, J=7.8, 8H).

Embodiment 10: Synthesis of the Representative Compound of Component A-10 (Component A-10.1; h=350)

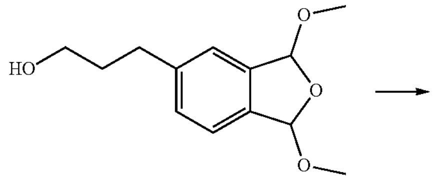

Compound 14

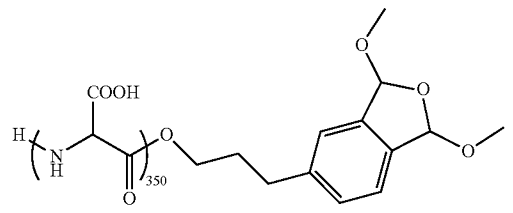

+

Compound 15

-continued

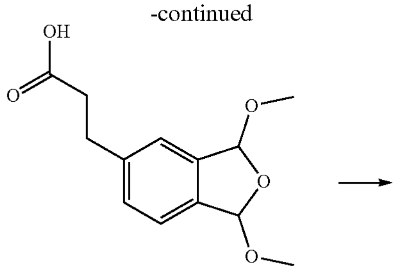

Compound 9

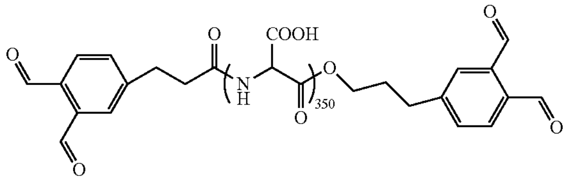

Compound A-10.1

(1) Synthesis of Compound 14: Compound 1 (2.0 g) was dissolved in anhydrous THF. Add lithium aluminum hydride (0.43 g) into above solution in batches at ice bath. The solution was stirred at 0 °C for 1 h. Quench the reaction by adding water, extract residual compounds with EA for three times and collect the organic phase. The organic phase was dried by anhydrous $Na_2SO_4$ and the solvent was removed by vacuum distillation to collected crude products, which were purified by silica gel column chromatography to obtain Compound 14 (1.43 g, yield: 80%). $^1H$ NMR (400 MHz, $CDCl_3$) δ=7.32 (m, 2H), 7.20 (s, 1H), 6.30 (s, 1H), 6.01 (s, 1H), 3.43 (m, 6H), 3.00 (t, J=7.7, 2H), 2.63 (t, J=7.7, 2H), 1.80 (m, 2H).

(2) Synthesis of Compound 15: Polyaspartic acid (8 g) was dissolved in anhydrous DMF (100 mL), with the addition of EDC (0.154 g), DMAP (0.0006 g) and Compound 2 (0.154 g). The solution was stirred at room temperature for 12 h. Remove the solvent by vacuum distillation after reaction completed. The mixture was redissolved in deionized water, dialyzed to remove small molecular impurities, and lyophilized to obtain light yellow solid (i.e., compound 15; 7.2 g, yield: 90%). According to $^1H$ NMR spectroscopy, the peaks at 7.2 and 7.3 ppm belong to the proton in benzene ring and the grafting degree (0.8-0.9) can be calculated by the integral ratio between above peaks and the peaks of protons in poly (ethylene glycol) skeleton. $^1H$ NMR (400 MHz, $D_2O$) δ=3.85 (S, 700H), 10.57 (s, 1H), 10.48 (s, 1H), 7.32 (m, 2H), 7.20 (s, 1H), 3.00 (t, J=7.7, 2H), 2.63 (t, J=7.7, 2H), 1.80 (m, 2H).

(3) Synthesis of Component A-10.1: Compound 15 (7.2 g) was dissolved in anhydrous DMF (100 mL), with the addition of benzotriazol-1-yl-oxytripyrrolidino-phosphonium hexafluorophosphate (PyBOP; 0.743 g), TEA (0.144 g) and compound 9 (0.294 g). The solution was stirred at room temperature for 12 h. Remove the solvent by vacuum distillation after reaction completed. The mixture was redissolved in deionized water, dialyzed to remove small molecular impurities, and lyophilized. The product was redissolved in anhydrous DMF with 10% TFA. The above solution was stirred at room temperature for 12 h. Remove TFA by vacuum distillation. The residue was redissolved in deionized water, dialyzed to remove small molecular impurities, and lyophilized to obtain light yellow solid (i.e., Component A-10.1; 7.2 g, yield: 90%). According to $^1H$ NMR spectroscopy, the peaks at 7.2 and 7.3 ppm belong to the proton in benzene ring, and the grafting degree (1.6-1.8) can be calculated by the integral ratio between above peaks and the peaks of protons in poly (ethylene glycol) skeleton. $^1H$ NMR (400 MHz, $D_2O$): δ=3.85 (s, 700H), 10.57 (s, 2H), 10.48 (s, 2H), 7.32 (m, 4H), 7.20 (s, 2H), 3.00 (t, J=7.7, 4H), 2.65 (t, J=7.7, 4H).

Contrast embodiment 11: The structure of a poly (ethylene glycol) derivative referred to in Chinese Patent CN202010454896.6 (as the control group of this invention).

Control component

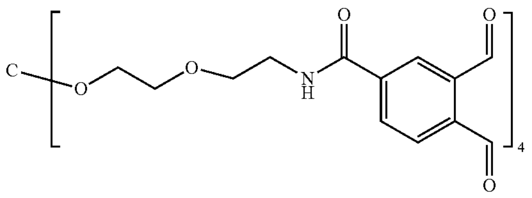

Embodiment 12: The Composition of Hydrogels

At 37 °C, various hydrogel precursor solutions can be prepared according to the method reported in this invention, as shown in Table 1.

TABLE 1

| | Amino-terminated four-arm PEG, 20 kDa (Component B-1) | Polylysine (Component B-2) | Hydrazide-modified hyaluronic acid, 340 kDa (Component B-3) |
|---|---|---|---|
| Component A-1.1 | A: 0.5-20 wt % B: 0.1-20 wt % | A: 0.5-20 wt % B: 0.1-20 wt % | A: 0.5-20 wt % B: 0.1-20 wt % |
| Component A-2.1 | A: 0.5-20 wt % B: 0.1-20 wt % | A: 0.5-20 wt % B: 0.1-20 wt % | A: 0.5-20 wt % B: 0.1-20 wt % |
| Component A-3.1 | A: 0.5-20 wt % B: 0.1-20 wt % | A: 0.5-20 wt % B: 0.1-20 wt % | A: 0.5-20 wt % B: 0.1-20 wt % |
| Component A-4.1 | A: 0.5-20 wt % B: 0.1-20 wt % | A: 0.5-20 wt % B: 0.1-20 wt % | A: 0.5-20 wt % B: 0.1-20 wt % |
| Component A-5.1 | A: 0.5-20 wt % B: 0.1-20 wt % | A: 0.5-20 wt % B: 0.1-20 wt % | A: 0.5-20 wt % B: 0.1-20 wt % |
| Component A-6.1 | A: 0.5-20 wt % B: 0.1-20 wt % | A: 0.5-20 wt % B: 0.1-20 wt % | A: 0.5-20 wt % B: 0.1-20 wt % |
| Component A-7.1 | A: 0.5-20 wt % B: 0.1-20 wt % | A: 0.5-20 wt % B: 0.1-20 wt % | A: 0.5-20 wt % B: 0.1-20 wt % |
| Component A-8.1 | A: 0.5-20 wt % B: 0.1-20 wt % | A: 0.5-20 wt % B: 0.1-20 wt % | A: 0.5-20 wt % B: 0.1-20 wt % |
| Component A-9.1 | A: 0.5-20 wt % B: 0.1-20 wt % | A: 0.5-20 wt % B: 0.1-20 wt % | A: 0.5-20 wt % B: 0.1-20 wt % |
| Component A-10.1 | A: 0.5-20 wt % B: 0.1-20 wt % | A: 0.5-20 wt % B: 0.1-20 wt % | A: 0.5-20 wt % B: 0.1-20 wt % |

In Table 1, wt % indicates the solid content of the solution. A preferred range of mass concentration for the hydrogel precursor solution is shown.

Mix A and B to obtain a series of hydrogels with various component proportions. Hydrogels with different compositions possess different mechanical properties and biological effects, thus being selected for different applications.

Embodiment 13: The Degradation Test of Hydrogels

TABLE 2

| No. | Formula |
|---|---|
| 1 | A-1.1/B-1 (2 wt %/1 wt %) |
| 2 | A-3.1/B-1 (2 wt %/1 wt %) |
| 3 | A-4.1/B-1 (2 wt %/1 wt %) |
| 4 | A-8.1/B-1 (2 wt %/1 wt %) |
| 5 | A-9.1/B-1 (2 wt %/1 wt %) |
| 6 | A-10.1/B-1 (2 wt %/1 wt %) |
| 7 | A-1.1/B-3 (2 wt %/1 wt %) |
| 8 | A-3.1/B-3 (2 wt %/1 wt %) |
| 9 | A-4.1/B-3 (2 wt %/1 wt %) |
| 10 | A-8.1/B-3 (2 wt %/1 wt %) |
| 11 | A-9.1/B-3 (2 wt %/1 wt %) |
| 12 | A-10.1/B-3 (2 wt %/1 wt %) |
| 13 | Control component/B-1 (2 wt %/1 wt %) |
| 14 | Control component/B-3 (2 wt %/1 wt %) |

To prove the excellent degradability of hydrogels prepared in this invention, we evaluate in vitro degradation of the hydrogels prepared on the basis of Table 2. The specific experimental method is as follows: Solution A and solution B in Table 2 are sprayed into a specially designed silicone tube by a mixing applicator with dual-catheter. The hydrogel was cured for 10 minutes and cut into cylindrical gel with similar volume using a surgical blade. Then, weigh the above gel pieces and transfer them into a 50 mL centrifuge tube. Add Dulbecco's phosphate buffered saline (DPBS) (pH=7.4, preheated to 37±1 °C), and shake the centrifuge tube at 37±1 °C. (60 r/min). Every 12 h, these samples were carefully collected, and gently blotted with filter paper to get rid of excess water on the surface. Continue the experiment until the sample cannot be collected completely. Record the degradation time and degradation rate. The degradation rate was calculated according to following equation:

$$\text{Degradation rate}=(\text{sample mass after degradation}/\text{sample mass before degradation})\times 100\%$$

Figure 2:
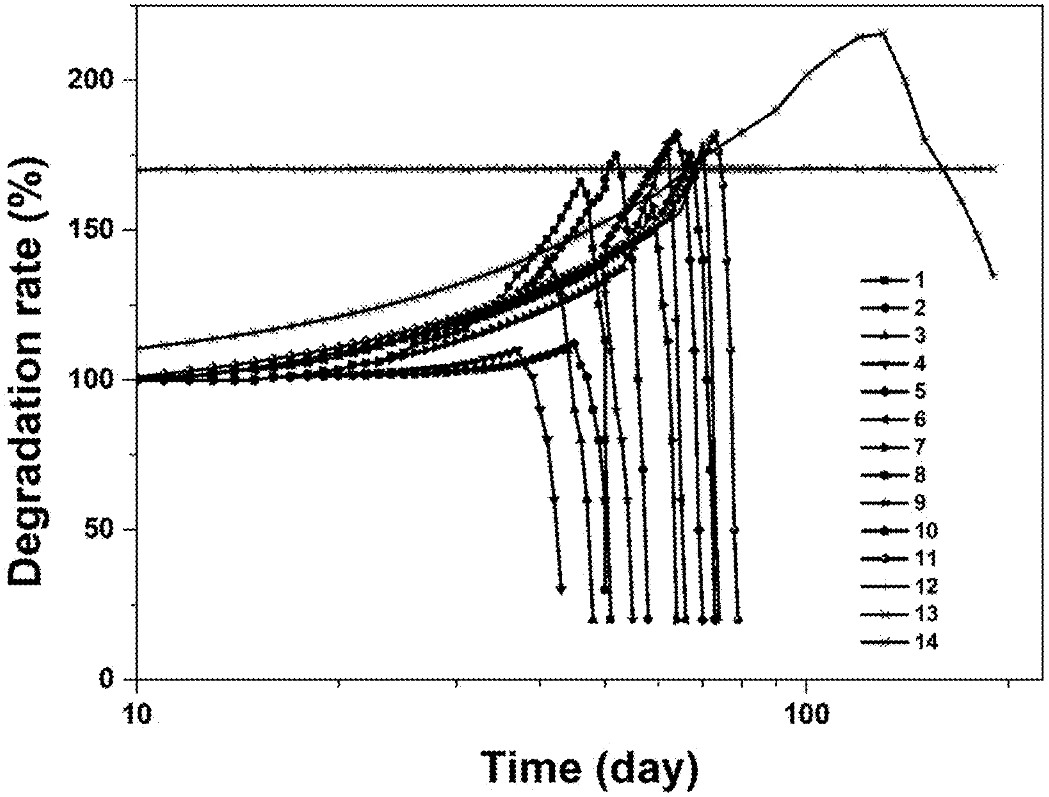
FIG. 2 is the degradation curve of hydrogels prepared in Embodiment 13.

By conducting above test, the degradation curve of the hydrogel is obtained in FIG. 2. The results indicate that, by introducing degradable structures into the polymer skeleton of aldehyde components, the hydrogels prepared in this invention have excellent degradability. For the hydrogels without introduction of degradable structures, their degradability depends on the amino component. When the amino component was the poly (ethylene glycol) with undegradable skeleton, the obtained hydrogels did not degrade (No. 13). When the amino component was hyaluronic acid with high molecular weight, the hydrogel exhibited a slow degradation rate (No. 14).

Figure 3:
FIG. 3 is the results of experimental group (right), which was treated with the hydrogel prepared in Embodiment 14, and the control group (left) after cervical surgery.

Embodiment 14: The Degradable Hydrogel for Promoting Repair After Cervical Surgery In the experiment, New Zealand female white rabbits were used to construct a cervical injury model. The rabbits were divided into two groups: the degradable hydrogel (Formula 11) treated group (group a), and untreated control group (group b). In the experiment, two excisional wounds were created on the left and right sides of the cervix of New Zealand female white rabbits by an electric knife. The hydrogel precursor solution was applied to the right wound by a mixing applicator with dual-catheter, and left wound was untreated. The repair results of the cervix were observed after 14 days. The wound healing with hydrogel treated is obviously faster than that of the blank group. The hydrogel treated wound healed completely, and the hydrogel has been completely degraded (right side of FIG. 3), while the blank group was still congested (left side of FIG. 3).

Other hydrogel compositions can also be applied for promoting repair after cervical surgery.

Embodiment 15: The Degradable Hydrogel for Preventing Postoperative Peritoneal Adhesion In the experiment, SD rats were used to construct a peritoneal adhesion model of abdominal wall-cecum scraping. The rats were divided into two groups: the degradable hydrogel (Formula 8) treated group (group a), and the poly (lactic acid) anti-adhesion film treated group (group b). During the surgery, the hydrogel precursor solution was sprayed to the wound site of the cecum and abdominal wall by a mixing applicator with dual-catheter. The obtained hydrogel was fixed at the wound site, achieving complete gelation within 1 min. In group b, the poly (lactic acid) anti-adhesion film was fixed to the wound by a commercially available adhesive. After 14 days, execute and dissect animals. Both groups did not show abdominal wall or cecum adhesion in the SD rats. In group a, the hydrogels were completely degraded, while there was no obvious degradation in group b. Therefore, the degradable hydrogel in this invention can prevent postoperative peritoneal adhesion and avoid the risk of material residues.

Other hydrogel compositions can also be applied for preventing postoperative peritoneal adhesion.

Embodiment 16: The Degradable Hydrogel for Intestinal Leakage Sealing

New Zealand male white rabbits were used and divided into three groups for cecal leakage sealing experiments: the degradable hydrogel (Formula 6) treated group (group a), the hydrogel (Formula 13), which was referred to in Chinese Patent CN202010455951.3, treated group (group b) and untreated control group (group c). In the experiment group, a model of leakage was made in the rabbit cecum. In group a and b, the hydrogel precursor solutions were applied to the wound by a mixing applicator with dual-catheter, both of which can seal the leakage. The leakage in group c was left untreated. Three weeks after the surgery, the rabbits were sacrificed by intravenous injection of air, and the cecum was extracted to evaluate the repairing effect. The results show that severe leakage occurred in the cecum without treatment (group c), while there was no leakage of the cecum in group a and b. The hydrogels were completely degraded in group a, while there was no obvious degradation in group b. Therefore, the hydrogel in this invention can not only effectively seal intestinal leakage but also avoid the risk of material residues.

Other hydrogel systems with different compositions can also be applied for intestinal leakage sealing.

Embodiment 17: The Degradable Hydrogel for Hepatic Hemostasis

Figure 4:
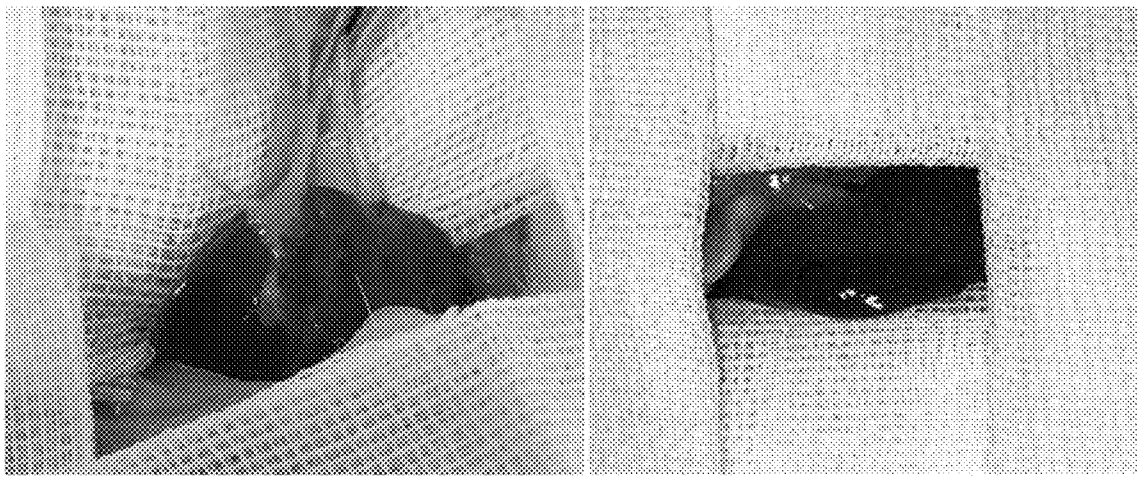
FIG. 4 is the results of hepatic hemostasis in the experimental group (right), which was treated with the hydrogel prepared in Embodiment 1, and the control group (left).

The SD rats were used and divided into two groups for the liver hemostasis experiments: the degradable hydrogel (Formula 5) treated group (group a), and the untreated control group (group b). In the experiment, after deep anesthesia, the rat's anterior chest was shaved with a shaver and the iodine was used to disinfect them. Cut an incision with a length of approximate 4 cm along the midline of the chest, open the chest and expose the liver. Make an incision with a diameter of approximate 2 cm in the left lobe of the liver. In group a, the hydrogel precursor solution was sprayed at the incision by a mixing applicator with dual-catheter, achieving gelation and hemostasis within 1 min. In group b, without any treatment, the liver incision oozed naturally and then coagulated. In group a, the hydrogel precursor solution at the incision was complete gelled, and the liver was placed back into the chest and sutured. Group b was directly sutured without any treatment. After 21 days, the liver recovery of SD rats was evaluated. The thoracic cavity was opened along the midline, and the liver recovery of the two groups of rats was photographed. The specimens were subjected to H&E staining, and photographs were taken with an optical microscope. The experimental results showed that the liver in group a recovered well, with the hydrogel completely degraded; no adhesion occurred, and new liver tissue has emerged at the liver incision (right side of FIG. 4). The adhesion between the liver and the omentum were observed in group b (left side of FIG. 4). Therefore, the hydrogel in this invention can not only be applied for liver hemostasis but also avoid the risk of material residues.

Other hydrogel systems with different compositions can also be applied for liver hemostasis.

Embodiment 18: The Degradable Hydrogel for Cardiac Hemostasis

Beagle dogs were used to construct a model of cardiac hemorrhage with 10 mL syringe needles and divided into two groups: the degradable hydrogel (Formula 2) treated group (group a) and fibrin glue treated group (group b). In group a, the hydrogel precursor solution was sprayed at the leak by a mixing applicator with dual-catheter, achieving gelation and hemostasis within 30 s.

Figure 5:
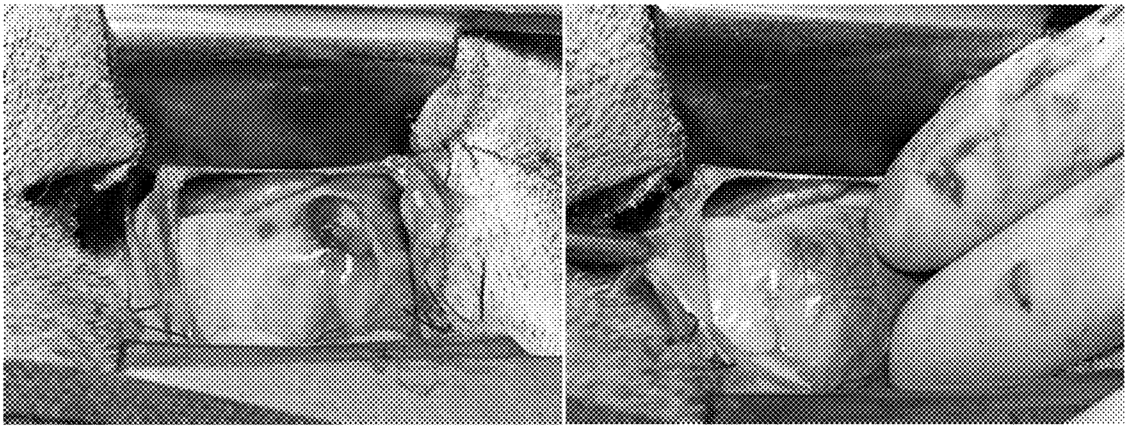
FIG. 5 is the results of cardiac hemostasis with the hydrogel prepared in Embodiment 18 (right) and with the fibrinogen glue (left).

In group b, fibrin glue was applied to stop bleeding. Due to the slow gelation rate and insufficient strength, the hemostatic material of group b cannot achieve hemostasis of cardiac hemorrhage (left side of FIG. 5), and the animals were sacrificed directly after surgery. By contrast, the degradable hydrogel in this invention can quickly stop heart bleeding, presumably because of its excellent tissue adhesion and strength (right side of FIG. 5). One week after the operation, the animals were sacrificed and dissected, and the heart site was well sealed without tissue necrosis.

Other hydrogel compositions can also be applied for cardiac hemostasis.

Embodiment 19: The Degradable Hydrogel for Dura Mater Spinalis Wound Repair

Beagle dogs were used and divided into two groups for dura mater spinalis wound repair experiment: the degradable hydrogel (Formula 5) treated group (group a); the hydrogel (Formula 13), which was referred to in Chinese Patent CN202010455951.3, treated group (group b). After the beagle dogs were anesthetized, open the back to expose the spinal dura mater under the spine and make a 2 mm gap in the dura mater spinalis to create spontaneous spinal fluid leakage. Then, the two hydrogel precursor solutions were sprayed at the gap by a mixing applicator with dual-catheter, both of which can seal the leakage. Four weeks after the operation, the animals were sacrificed and dissected. In two groups, both wounds of the beagle dogs healed, and there was no further leakage of spinal fluid. The hydrogels in group a were completely degraded, while the hydrogel in group b were not significantly degraded. The results prove that the degradable hydrogel in this invention can be applied for dura mater spinalis wound repair with a suitable degradation time.

Other hydrogel systems with different compositions can also be applied for dura mater spinalis wound repair.

Embodiment 20: The Degradable Hydrogel for Dura Mater Wound Repair

Beagle dogs were used and divided into two groups for dura mater wound repair experiment: the degradable hydrogel (Formula 4) treated group (group a); the hydrogel (Formula 13), which was referred to in Chinese Patent CN202010455951.3, treated group (group b). After the beagle dogs were general anesthetized, make a curved incision in the left forehead parietal region and make a 2 mm gap in the dura mater to create spontaneous cerebrospinal fluid leakage. both of the two hydrogel precursor solutions were sprayed at the gap by a mixing applicator with dual-catheter, and both of them can seal the leakage. After 30 days, the animals were sacrificed and dissected. In two groups, both wounds of the beagle dogs healed, and there was no further cerebrospinal fluid leakage. The hydrogels in group a were completely degraded, while the hydrogel in group b were not significantly degraded. The results show that the degradable hydrogel in this invention can be applied for dura mater wound repair with a suitable degradation time.

Other hydrogel systems with different compositions can also be applied for dura mater wound repair.

Embodiment 21: The Degradable Hydrogel for Blood Vessels Sealing

The male beagle dogs were used to evaluate the ability of the hydrogel for sealing the blood vessels. The dogs were divided into two groups: the hydrogel (Formula 1) treated group (group a); the suture group (group b). After the beagle dog was anesthetized and blood heparinized, separate the subcutaneous connective tissue to expose the artery, then strip the adipose tissue around the artery. The arterial vessel was clamped by atraumatic vascular clamps, and the artery was perforated with a 27-gauge needle. In group a, the hydrogel precursor solutions were sprayed at the wound by a mixing applicator with dual-catheter, achieving gelation and hemostasis within 1 min. In group b, the wound was sutured with surgical thread. The atraumatic vascular clamps were removed in both groups at the same time. There was no bleeding occurred in group a, while there was bleeding occurred in group b. Three weeks after the surgery, the animals were sacrificed and dissected. In two groups, both wounds of the beagle dogs healed, and there was no further bleeding. The hydrogels in group a were completely degraded. The results prove that the hydrogel in this invention can achieve sealing of vascular hemorrhage with a suitable degradation time.

Other hydrogel systems with different compositions can also be applied for blood vessels sealing.

The above embodiments intend to facilitate the understanding and use of the invention. It is obvious that operators can easily make various modifications to these embodiments and the general principles described herein can be applied to other embodiments. Therefore, the invention is not limited to the embodiments described above. If the modifications and changes were not departing from the scope of this invention, they shall be under protection of this invention.

What is claimed is:

1. A o-phthalaldehyde modified degradable polymer having a structure selected from the following structures of Components A-1 to A-3:

Component A-1

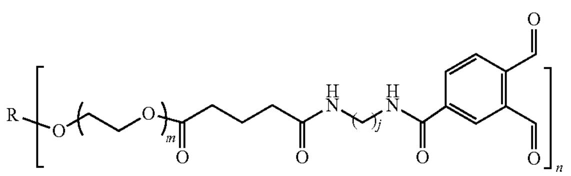

Component A-2

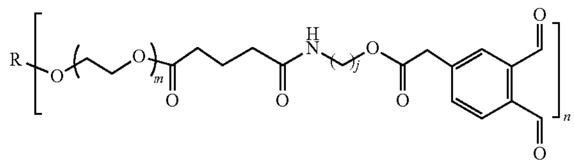

Component A-3

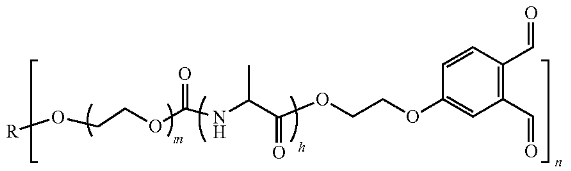

in the above structures, j, m and h represent the numbers of repeating units, $1\leq j\leq 30$, $5\leq m\leq 1000$, $2\leq h\leq 1000$;

n represents a branching degree of multi-arm polymer, and n is selected from 2, 3, 4, 5, 6, or 8;

wherein:

when n=2, R is a two-arm branching center and selected from one of the following structures:

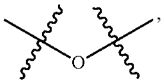,
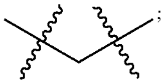;

when n=3, R is a three-arm branching center and selected from one of the following structures:

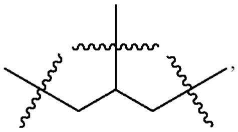,
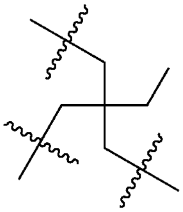,
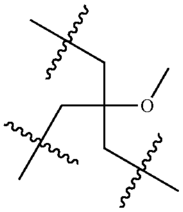;

when n=4, R is a four-arm branching center and selected from one of the following structures:

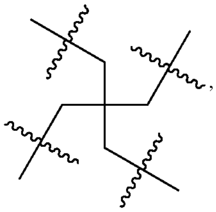,
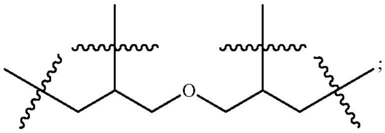;

when n=5, R is a five-arm branching center and selected from one of the following structures:

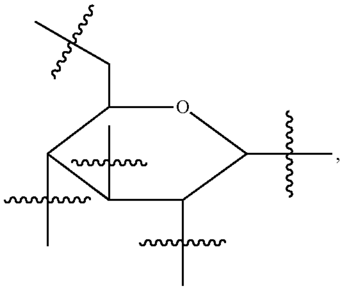,
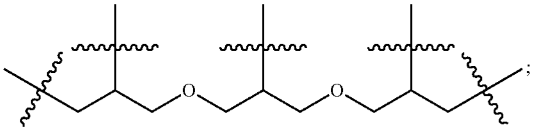;

when n=6, R is a six-arm branching center and selected from one of the following structures;

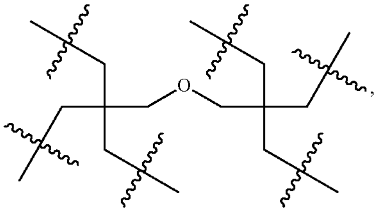,
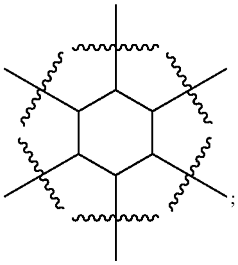;

and when n=8, R is an eight-arm branching center and selected from one of the following structures:

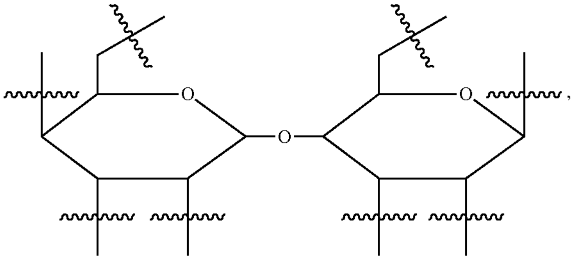,
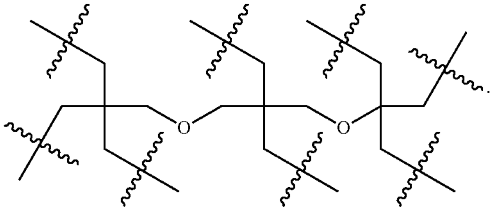.

2. A degradable dual-component hydrogel prepared by mixing a component A, a component B, and a solvent;

wherein the component A is the o-phthalaldehyde modified degradable polymer according to claim 1;

the component B is a water-soluble small molecule, a water-soluble synthetic polymer or a polysaccharide that contains one or more types of groups selected from primary amine, hydrazine, hydrazide, hydroxylamine, and sulfhydryl, with a number of the groups not less than 2.

3. The degradable dual-component hydrogel according to claim 2, the component B is selected from an amino acid compound containing multiple amino groups, lysine-modified two-arm or multi-arm poly (ethylene glycol), amino-terminated two-arm or multi-arm poly (ethylene glycol), lysine-modified hyaluronic acid, hydrazide-modified hyaluronic acid or hydrazide-modified chitosan.

4. The degradable dual-component hydrogel according to claim 2, the solvent is selected from water, physiological saline, buffer solution, acellular matrix, or cell culture medium solution.

5. A preparation method of the degradable dual-component hydrogel according to claim 2, comprising:

dissolving the component A and the component B in the solvent to obtain a solution A and a solution B, respectively; and mixing the solution A and the solution B to obtain a hydrogel.

6. The preparation method according to claim 5, wherein:

in the solution A, a solid content of the component A is 0.5-20 wt %, and in the solution B, a solid content of the component B is 0.1-20 wt %.

7. The degradable dual-component hydrogel according to claim 2, wherein applications of the degradable dual-component hydrogel are selected from:

a use of the degradable dual-component hydrogel for preparing repair-promoting materials after cervical surgery;

a use of the degradable dual-component hydrogel for preparing materials to prevent postoperative peritoneal adhesion;

a use of the degradable dual-component hydrogel for preparing materials to seal intestinal leakage;

a use of the degradable dual-component hydrogel for preparing hepatic hemostatic materials;

a use of the degradable dual-component hydrogel for preparing cardiac hemostatic materials;

a use of the degradable dual-component hydrogel for preparing materials to repair dura mater spinalis wound;

a use of the degradable dual-component hydrogel for preparing materials to repair dura mater wound;

a use of the degradable dual-component hydrogel for preparing materials to seal blood vessels.

* * * * *